United States Patent
Yui et al.

(10) Patent No.: US 7,041,310 B2
(45) Date of Patent: May 9, 2006

(54) PHARMACEUTICAL PREPARATION FOR THE TREATMENT OF GYNECOLOGICAL DISEASES

(75) Inventors: Nobuhiko Yui, 4-103, Matsugaoka, Tatsunokuchi-machi, Nomi-gun, Ishikawa-ken (JP); Kouichi Murakami, Kanazawa (JP); Tooru Ooya, Tsurugi-machi (JP); Ikuo Sato, Yokohama (JP)

(73) Assignees: Chisso Corporation, Osaka (JP); Nobuhiko Yui, Ishikawa-ken (JP)

( * ) Notice: Subject to any disclaimer, the term of this patent is extended or adjusted under 35 U.S.C. 154(b) by 368 days.

(21) Appl. No.: 10/108,298

(22) Filed: Mar. 28, 2002

(65) Prior Publication Data

US 2002/0150605 A1 Oct. 17, 2002

(30) Foreign Application Priority Data

Mar. 30, 2001 (JP) .................................. 2001-100426

(51) Int. Cl.
*A61F 6/06* (2006.01)
*A61F 6/14* (2006.01)
*A61F 13/02* (2006.01)

(52) U.S. Cl. .................... 424/430; 424/431; 424/432; 424/433

(58) Field of Classification Search ................ 424/430, 424/431, 432, 433
See application file for complete search history.

(56) References Cited

U.S. PATENT DOCUMENTS

| | | |
|---|---|---|
| 4,851,521 A | 7/1989 | della Valle et al. |
| 5,462,976 A | 10/1995 | Matsuda et al. |
| 5,644,049 A | 7/1997 | Giusti et al. |
| 5,679,657 A | 10/1997 | Oka et al. |
| 6,066,340 A * | 5/2000 | Callegaro et al. ........... 424/499 |
| 6,673,919 B1 * | 1/2004 | Yui et al. .................... 536/124 |

FOREIGN PATENT DOCUMENTS

| | | |
|---|---|---|
| EP | 0 330 786 A1 | 9/1989 |
| EP | 0 609 042 A1 | 8/1994 |
| JP | 07-309902 | 11/1995 |
| JP | 08-053501 | 2/1996 |
| JP | 2590358 | 12/1996 |
| WO | WO 97/18244 | 5/1997 |
| WO | WO02/18450 A1 | 3/2002 |

OTHER PUBLICATIONS

Maria Rochira et al.; "Novel Vaginal Delivery System for Calcitonin II. Preparation and Characterization of HYAFF Microspheres Containing Calcitonin"; International Journal of Pharmaceutics 144 (1996) pp. 19–26.

Yui et al., "Chemically Modified Hyaluronic Acid or Salts Thereof, and a Process for Producing Thereof", U.S. Appl. No. 10/107,195, filed Mar. 28, 2002, pending.

* cited by examiner

*Primary Examiner*—Carlos A. Azpuru
(74) *Attorney, Agent, or Firm*—Leydig, Voit & Mayer, Ltd.

(57) ABSTRACT

This invention provides to a novel pharmaceutical preparation for the treatment of gynecological diseases. The pharmaceutical preparation according to the invention comprises a therapeutic drug for the intrauterine, intravaginal or intrapelvic administration, or for the administration into the ovarian endometrioma, and a biodegradable polymer comprising a chemically modified hyaluronic acid or a salt thereof prepared by O-acylating, alkoxylating or crosslinking a complex of hyaluronic acid or a salt thereof and a cationic compound in a nonaqueous solvent. The preparation of the invention is preferably administered intrauterine, intravaginal, intrapelvic, and intratumor cavity.

12 Claims, No Drawings

PHARMACEUTICAL PREPARATION FOR THE TREATMENT OF GYNECOLOGICAL DISEASES

FIELD OF THE INVENTION

This invention relates to a novel pharmaceutical preparation for the treatment of gynecological diseases. More specifically, the invention relates to a pharmaceutical preparation for the treatment of gynecological diseases, which comprises a therapeutic drug for the intrauterine, intravaginal or intrapelvic administration or for the administration into the ovarian endometorioma and a chemically modified hyaluronic acid or a salt thereof and wherein the drug is supported by the chemically modified hyaluronic acid or a salt thereof, and to use of the chemically modified hyaluronic acid or a salt thereof for manufacturing the pharmaceutical preparation for the treatment of gynecological diseases.

BACKGROUND OF THE INVENTION

When a long-term effect of a therapeutic drug for the intrauterine, intravaginal or intrapelvic administration or for the administration into the ovarian endometrioma is required, the drug has to be employed as a pharmaceutical preparation wherein the drug is supported by a carrier.

For instance, a drug for the treatment of endometriosis, such as danazol or Gm-RH analogues, has been orally or subcutaneously administered. In these cases, however, patients have frequently been subjected adverse effects such as liver functional impairment, weight gain, sterility, menstrual disorder, dropsy, hot flush, shoulder stiffness, headache and osteoporosis. The Japanese Patent No. 2590358 discloses a preparation for the intrauterine device, in which danazol as a drug for the treatment of endometriosis is supported by silicone as a carrier in order to avoid those adverse effects.

Regarding the aforementioned preparation, however, a releasing efficiency of the drug from silicone is insufficient. Further, there is concern with the adverse effect of the silicone carrier for the uterus. Since the silicon carrier remains in the uterus after the completion of the release of the drug, it is necessary to remove the silicone carrier from the uterus and thus patients are subjected to the physical or mental burden.

DISCLOSURE OF THE INVENTION

An object of the present invention is to provide a pharmaceutical preparation for the treatment of gynecological diseases, wherein a carrier has a superior sustained releasing property of a drug to be administered and needs not to be removed from the uterus after the treatment. Another object of the invention is to provide use of a carrier for manufacturing the pharmaceutical preparation for the treatment of gynecological diseases.

We have intensively studied the aforementioned problems of the prior art and found that a therapeutic drug for the intrauterine, intravaginal or intrapelvic administration, or for the administration into the ovarian endometrioma is effectively released from a pharmaceutical preparation wherein the drug is supported by the biodegradable polymer as a carrier, especially hyaluronic acid or a salt thereof.

We also found that a chemically modified hyaluronic acid or a salt thereof prepared by O-acylating, alkoxylating or crosslinking a complex of hyaluronic acid or a salt thereof and a cationic compound in a nonaqueous solvent maintains a superior sustained releasing property of a drug in the body for a long term. Furthermore, a carrier comprising the chemically modified hyaluronic acid or a salt thereof according to the present invention contains a reduced amount of a pyrogen and an antigenic substance. Thus, there is concern with an adverse effect and its safety is ensured.

If the pharmaceutical preparation according to the invention is directed to the intrauterine, intravaginal or intrapelvic administration or the administration into the ovarian endometrioma, a carrier according to the invention needs not be removed from the uterus after the completion of the release of the drug and thus physical and mental burden of patients are significantly decreased.

In consideration of the above, we complete a pharmaceutical preparation for the insertion into the uterine cavity or vagina, which has a superior sustained releasing property of a therapeutic drug for the treatment of gynecological diseases.

The present invention are defined in the following items (1) to (18).

(1) A pharmaceutical preparation for the treatment of gynecological diseases which comprises a therapeutic drug for the intrauterine, intravaginal or intrapelvic administration, or for the administration into the ovarian endometrioma and a biodegradable polymer comprising hyaluronic acid or a salt thereof and wherein the drug is supported by the biodegradable polymer as a carrier.

(2) The pharmaceutical preparation as defined in item (1), in which the biodegradable polymer is a chemically modified hyaluronic acid or a salt thereof.

(3) The pharmaceutical preparation as defined in item (1), in which the biodegradable polymer is a chemically modified hyaluronic acid or a salt thereof prepared by O-acylating, alkoxylating or crosslinking a complex of hyaluronic acid or a salt thereof and a cationic compound in a nonaqueous solvent.

(4) The pharmaceutical preparation as defined in item (3), in which the cationic compound is a quaternary ammonium salt.

(5) The pharmaceutical preparation as defined in item (3), in which the nonaqueous solvent is one or more solvents selected from the group consisting of chloroform, toluene, methylene chloride and heptane.

(6) The pharmaceutical preparation as defined in item (3), wherein an amount of a pyrogen and/or an antigenic substance in the chemically modified hyaluronic acid or a salt thereof is decreased by O-acylating, alkoxylating or crosslinking the complex in the nonaqueous solvent.

(7) The pharmaceutical preparation as defined in item (6), wherein the amount of the pyrogen is not more than 0.05 endotoxin unit (EU)/mg.

(8) The pharmaceutical preparation as defined in item (1), in which the O-acylating reaction for the production of the biodegradable polymer is a reaction with an organic acid employing at least one acid catalyst selected from the group consisting of mineral acids, organic acids and Lewis acids, a reaction with an organic acid employing at least one dehydrating agent selected from the group consisting of N,N'-dicyclohexylcarbodiimide, 2-chloro-1-methyl pyridiniumiodide and N,N'-carbonyl diimidazole, or an O-acylation employing an acid anhydride or an acid halide in the presence of an acid binder.

(9) The pharmaceutical preparation as defined in item (1), in which the alkoxylating reaction for the production of the biodegradable polymer is an alkoxylation using an alkyl halide or an alkoxide in the presence of an acid binder, or an alkoxylation by the dehydration of hydroxyl groups using Brönsted acid or Lewis acid as an acid catalyst.

(10) The pharmaceutical preparation as defined in item (1), in which the crosslinking reaction comprises irradiating a certain wavelength of light to the chemically modified hyaluronic acid or a salt thereof into which a photoreactive group has been introduced.

(11) The pharmaceutical preparation as defined in item (1), in which the crosslinking reaction is an auto-crosslinking reaction using no crosslinking agent or a reaction using at least one crosslinking agent selected from the group consisting of polyfunctional aldehydes, polyfunctional epoxy compounds and polyhydric alcohols.

(12) The pharmaceutical preparation as defined in item (1), wherein a weight ratio of the drug to the biodegradable polymer is in the range of 1:10 to 2:1.

(13) The pharmaceutical preparation as defined in item (1), which is a T-shaped preparation and wherein a vertical bar has a length of 20 to 40 mm and a diameter of 1.0 to 3.0 mm and wherein a transverse bar has a length of 25 to 45 mm and a diameter of 3.0 to 4.0 mm.

(14) The pharmaceutical preparation as defined in item (1), which is a IUD-like ring preparation and wherein an outside diameter is in the range of 20 to 40 mm and a thickness is in the range of 2.5 to 4.5 mm.

(15) The pharmaceutical preparation as defined in item (1), which is a sheet gel.

(16) The pharmaceutical preparation as defined in item (1), which is a spherical preparation and of which a diameter is in the range of 20 to 25 mm.

(17) The pharmaceutical preparation as defined in item (1), which is a paste gel.

(18) The pharmaceutical preparation as defined in item (1), wherein the drug is a therapeutic drug for endometriosis.

(19) The pharmaceutical preparation as defined in item (1), wherein the therapeutic drug is danazol.

(20) Use of a chemically modified hyaluronic acid or a salt thereof as a carrier for manufacturing the pharmaceutical preparation for the treatment of gynecological diseases, characterized in that the chemically modified hyaluronic acid or a salt thereof are prepared by O-acylating, alkoxylating or crosslinking a complex of hyaluronic acid or a salt thereof and a cationic compound in a nonaqueous solvent.

BEST MODE FOR CARRYING OUT THE INVENTION

The term "biodegradable polymer" used herein means a polymer which is degradable and/or absorbable in a mammal body including a human body. Examples of the biodegradable polymer include hyaluronic acid, chondroitin and sulfated polysaccharides such as heparin, heparan sulfate, chondroitin sulfate and dermatan sulfate and salts thereof, water soluble polysaccharides such as alginic acid, polygalacturonic acid, dextran and carboxymethyl chitin and salts thereof, proteins such as collagen, polyamino acids and salts thereof such as polyglutamic acid, and hydrophilic polymers such as polyethylene glycol, polyvinyl alcohols and the like, but not limited thereto. Furthermore, the aforementioned compounds which have been chemically modified may be included in the present invention. In this invention, a chemical modification may include organic synthetic modifications and enzymatic modifications, but not limited thereto.

When the pharmaceutical preparation for the treatment of endometriosis according to the present invention is prepared with at least one of the biodegradable polymer selected from the group consisting of polysaccharides such as hyaluronic acid, heparin, heparan sulfate, chondroitin, chondroitin sulfate and dermatan sulfate and salts thereof, alginic acid and a salt thereof, polygalacturonic acid and a salt thereof, proteins such as collagen and polyamino acids such as polyglutamic acid and salts thereof as a carrier, the intrauterine or intravaginal degradation of the carrier and the release of the therapeutic drug accompanied thereby are induced by the action of intrinsic hydrolytic enzymes and thus the improved delivery of drugs to the lesion will be expected.

Particularly, using hyaluronic acid or a salt thereof or a material principally comprising hyaluronic acid or a salt thereof as a carrier of the drug for the intrauterine or intravaginal administration, the intrauterine or intravaginal degradation of the carrier and the release of the therapeutic drug accompanied thereby highly correlate with intrinsic activity of hyaluronidase of a patient, and thus the improved delivery of drugs will be offered. Therefore, hyaluronic acid or a salt thereof is preferably employed in the present invention.

when hyaluronic acid or a salt thereof is employed as a carrier, it is not clearly confirmed that the rate or velocity of intrauterine or intravaginal degradation of the carrier and the release of the therapeutic drug accompanied thereby. However, the existence of a hyalutonate degrading enzyme such as hyaluronidase has been determined and an active oxygen in the uterus and the vagina has also been detected. These activities of degradation are changeable to the menstrual cycle and thus these changes are available for the effective release of the therapeutic drug.

A duration of the sustained release or the drug efficacy of the pharmaceutical preparation for the treatment of gynecological diseases according to the invention can be decided dependent on a patient's condition, a therapeutic purpose thereof or the like. The duration of the sustained release can be controlled by using a degradation rate of a biodegradable polymer employed in the invention and a surface area and volume of the pharmaceutical preparation. The degradation rate of a biodegradable polymer can be controlled by using properties of the biodegradable polymer such as species, structure and degree of the chemical modification, three dimensional structure, an average molecular weight or the like.

For instance, where a biodegradable polymer is the aforementioned chemically modified hyaluronic acid or a salt thereof, the resistance to the degradation by a hyalutonate degrading enzyme and an active oxygen can be provided to decrease the degradation rate or to prolong the duration of the sustained release. In this case, it is preferable to increase the degree of the intramolecular and intermolecular crosslinking of the chemically modified hyaluronic acid or a salt thereof by using a crosslinking agent.

If a drug to be supported is a hydrophobic compound such as danazol, it is possible to decrease the degradation rate or to prolong the duration of the sustained release using as a carrier a chemically modified hyaluronic acid or a salt thereof prepared by O-acylating, alkoxylating or crosslinking a complex of hyaluronic acid or a salt thereof and a cationic compound in a nonaqueous solvent.

Hyaluronic acid or a salt thereof employed in this invention may be derived from, but not limited to, various animal tissues such as a tissue of comb or microorganisms which are capable of producing hyaluronic acid. Hyaluronic acid or a salt thereof is preferably derived from the microorganisms.

Examples of the microorganisms capable of producing hyaluronic acid may include *Streptococcus pyogenes, Streptococcus equisimilis, Streptococcus equi, Streptococcus dysgalactiae, Streptococcus zooepidemicus* and the like.

An average molecular weight of the hyaluronates used in the present invention as a raw material, which is measured by the viscometry, is at least 10,000, preferably more than 100,000, more preferably in the range of 500,000 to 1,500,000.

Examples of the cationic compound used in the present invention may include quaternary ammonium salts, amino acids having two or more amino groups, peptides, salts of polyamino acids, salts of sugars having two or more amino groups, preferably quaternary ammonium salts.

Examples of the quaternary ammonium salts include distearyldimethylammonium chloride, dioleyldimethylammonium chloride, cetylpyridinium chloride, cetyltrimethylammonium chloride, cetyltrimethylammonium bromide, ditetradecyldimethylammonium bromide, didodecyldimethylammonium bromide, didecyldimethylammonium bromide, octadecyltrimethylammonium chloride, n-octadecyltrimethylammonium bromide, tridodecylmethylammonium chloride, trioctylmethylammonium bromide, dioctanoyl L-α-phosphatidylcholine, dilauroyl L-α-phosphatidylcholine, phosphatidylcholine, dipalmitoyl D,L-α-phosphatidylcholine, 1,2-dimyristoyl-3-trimethylammonium propane, 1,2-dioleoyl-3-trimethylammonium propane, 1,2-dipalmitoyl-3-trimethylammonium-propane, 1,2-distearoyl-3-trimethylammonium propane, benzalkonium chloride, benzethonium chloride and the like.

In the specification, the complex of hyaluronic acid or a salt thereof and the cationic compound means a complex in which an anionic moiety such as the carboxyl group of hyaluronic acid or a salt thereof and the cationic compound form an ionic-bond. An example of method for preparing the complex is illustrated below.

<Preparation of a Complex Consisting of the Hyaluronate and the Cationic Compound>

(A) The hyaluronate is dissolved in distilled water or purified water corresponding thereto at the concentration in the range of 0.01% to 10%, preferably 0.05% to 1%. In the present invention, "purified water corresponding to distilled water" means water purified, for example, with by the electric deionization and the reverse osmosis procedures.

(B) The cationic compound to be complexed with the hyaluronate, preferably the quaternary ammonium salt is added and dispersed in distilled water or corresponding purified water.

The solution of the hyaluronate prepared in (A) and the solution of the cationic compound prepared in (B) are mixed so that the molar ratio of the cationic group in the cationic compound to the carboxyl group in the hyaluronate is in the range of 0.5–5:1, preferably 0.7–1.5:1, for example 1:1.

The mixing may be performed at room temperature. Preferably, both the solutions are heated up to the gel-liquid crystal transition point temperature of the cationic compound and mixed at an temperature equal or higher than that temperature.

The insoluble product obtained by the mixing can be recovered from the mixture by a separation method conventionally employed in the art, for example, centrifugation, suction filtration, pressure filtration or the like. The insoluble product recovered is washed with water or purified water corresponding thereto which has been heated up to the gel-liquid crystal transition point temperature or higher and then subjected to drying. The drying can be carried out by means of any drying procedure conventionally employed in the art, e.g. atmospheric drying, vacuum drying, freeze drying or the like.

Examples of the nonaqueous solvents include chloroform, methylene chloride, toluene, heptane, ethanol, methanol, propylene glycol, ethylene glycol, dimethylformamide (DMF), dimethyl sulfoxide (DMSO), tetrahydrofuran (THF) and a mixed solvent thereof. The concentration of the complex consisting of the hyaluronate and the cationic compound is preferably in the range of 1 to 1000 mmol/L, but not limited thereto.

Examples of the O-acylation in the present invention may include (1) a reaction with an organic acid employing one or more acid catalysts, for example, mineral acids such as hydrochloric acid or sulfuric acid, organic acids such as aromatic sulfonic acid and Lewis acids such as boron fluoride etherate or the like, (2) a reaction with an organic acid employing one or more dehydrating agents, for example, N,N'-dicyclohexylcarbodiimide, 2-chloro-1-methyl pyridiniumiodide and N,N'-carbonyl diimidazole or the like, and (3) an O-acylation employing an acid anhydride or an acid halide, e.g. the Schotten-Baumann method in the presence of an acid binder, such as sodium acetate, triethylamine, pyridine, 4-dimethylamino pyridine or the like.

Examples of the alkoxylation in the invention may include (1) a reaction using an alkyl halide and an alkoxide, e.g. the Williamson reaction and (2) a dehydration of hydroxyl groups using Brönsted acid or Lewis acid as an acid catalyst.

Examples of the crosslinking reaction may include a photocrosslinking reaction by the irradiation such as gamma-ray irradiation, an auto-crosslinking reaction by adjusting pH of a solution containing hyaluronic acid or a salt thereof and optionally by repeating freeze-thaw, and a crosslinking reaction using as a crosslinking agent (1) polyfunctional aldehydes such as glutaraldehyde and terephthalaldehyde, (2) polyfunctional epoxy compounds such as epichlorohydrin, 1,2-bis(2,3-epoxypropoxy)ethane, ethyleneglycol diglycidyl ether or (3) polyhydric alcohols such as ethylene glycol and propylene glycol.

According to the present invention, a weight ratio of a therapeutic drug for the intrauterine, intravaginal or intrapelvic administration, or for the administration into the ovarian endometrioma to a biodegradable polymer (i.e. [Drug]/[Polymer]) is preferably in the range of 1/1000 to 10/1, more preferably in the range of 1/10 to 2/1. Within the range of the weight ratio, the therapeutic drug for the intrauterine, intravaginal or intrapelvic administration, or for the administration into the ovarian endometrioma can be effectively released from the pharmaceutical preparation according to the invention. When a double-layer preparation is manufacturing as mentioned below, the outer layer of the preparation is preferably in the aforementioned range of the weight ratio of the drug to the polymer.

The pharmaceutical preparation for the treatment of gynecological diseases according to the present invention can be manufactured by a process which comprises mixing a therapeutic drug for the intrauterine, intravaginal or intrapelvic administration, or for the administration into the ovarian endometrioma and a biodegradable polymer in powder form, dissolving or suspending the mixture in a solvent into which the polymer is soluble, pouring into a mold and removing the solvent.

In addition to the therapeutic drug for the treatment of gynecological diseases, the pharmaceutical preparation according to the present invention may include sugars, amino acids, peptides, proteins, enzymes, lipids, minerals, organic salts, metals or the like without the reduction in an effect of drugs.

When the preparation according to the present invention is directed to a preparation for inserting into the uterine cavity, the vagina, the pelvis or the ovarian endometrioma, the preparation has any form, shape and size suitable for the desired administration and is not particularly limited. The form thereof may be a solid, gel or liquid form. For the intrauterine administration, the shape thereof may be T-shaped form, intra uterine device-like ring (hereinafter referred to as "IUD-like ring"), sheet gel or the ring or paste gel. For the intrapelvic administration or the administration into the ovarian endometrioma, the shape may be a sheet gel or paste gel.

The size of the preparation according to the present invention may be varied dependent on a purpose of use or the subject to be administered. When a subject is human and the preparation of the invention is a T-shaped preparation, a length of a vertical bar of the preparation is in the range of 20 to 40 mm, preferably 30 to 35 mm and a length of a transverse is in the range of 25 to 45 mm, preferably 30 to 38 mm. A diameter of the vertical bar is in the range of 1.0 to 3.0 mm and a diameter of the transverse bar is in the range of 3.0 to 4.0 mm, preferably 3.2 to 3.6 mm.

When the preparation is a IUD-like ring, an outside diameter thereof is in the range of 20 to 25 mm and a thickness is in the range of 2.5 to 4.5 mm, preferably 3.0 mm.

When the preparation is a sheet gel preparation, a width thereof is in the range of 10 to 50 mm, preferably 20 to 30 mm, a length is in the range of 20 to 70 mm, preferably 40 to 60 mm and a thickness is in the range of 2 to 20 mm, preferably 5 to 10 mm.

When the preparation is a spherical gel preparation, a diameter thereof is in the range of 10 to 30 mm, preferably 20 to 25 mm. When the preparation is a ring preparation for the intravaginal administration, an outer diameter thereof is in the range of 30 to 60 mm, preferably 45 to 55 mm and a thickness of the ring is in the range of 4.0 to 12.0 mm, preferably 7.5 to 10.0 mm. In the case of a paste gel preparation, a size thereof is not particularly limited.

When the preparation according to the present invention is the T-shaped preparation or the IUD-like ring, the preparation may be composed of a monolayer or a double layer which includes a core of plastic or the like in order to increase the strength of the preparation.

When a core is used for manufacturing the T-shaped preparation for the intrauterine administration, the core is usually included in both the vertical and transverse bars. A length of the core is in the range of 55 to 70% of each bar and a diameter of the core is in the range of 60 to 90% of each bar. Further, the drug is deposited on the vertical bar. The T-shaped preparation for the intrauterine administration may be preferably attached a nylon monofilament at lower end of the vertical bar thereof. A length of the nylon monofilament is in the range of 30 to 400 mm, preferably 50 to 280 mm and a diameter thereof is in the range of 0.170 to 0.290 mm.

The ring preparation according to the present invention may be constructed as a monolayer or double layer ring in order to improve the release efficiency of the drug dependent on the desired duration of the treatment and the degree of symptoms to be treated. In the case of the double layer ring preparation for the intravaginal administration, a thickness of the outer layer is at least 0.1 mm, preferably in the range of 0.1 to 2.0 mm.

The pharmaceutical preparations for the treatment of gynecological diseases according to the present invention can be manufactured by conventional techniques employed for the manufacturing the preparations for the intrauterine, intravaginal or intrapelvic administration, or for the administration into the ovarian endometrioma. For instance, the monolayer preparation can be manufactured by a process which comprises transferring danazol and a base material of a carrier into a vessel placed in a clean bench, adding a crosslinking agent thereto, mixing the mixture for 20 to 30 minutes at room temperature, pouring the mixture into a mold and then hardening at room temperature. The amounts and weight ratio of danazol and a base material of the carrier are set within the aforementioned ranges. A mold suitable for the aforementioned shape and size of the preparation is also employed.

The double layer preparation can be manufactured in the same manner of the aforementioned manufacture of the monolayer preparation, except for embedding a desired core into the mold at the step for molding the obtained mixture. The aforementioned cores can be employed.

The preparations according to the present invention are required aseptic. Therefore, all steps of the manufacture are carried out under the sterile condition and the final preparations are packaged with a packaging material such as aluminum heat seal or the like.

According to the present invention, examples of a therapeutic drug for the intrauterine, intravaginal or intrapelvic administration, or for the administration into the ovarian endometrioma may include therapeutic drugs for endometriosis, contraceptives, antipyretics, hormone drugs, antihormone drugs, therapeutic drugs for endometrioid carcinoma, inhibitors of hormone synthesis, antibiotics, antifungal drugs, therapeutic drugs for vaginosis, therapeutic drugs for trichomoniasis, therapeutic drugs for cervical uterocervical cancer and the like, but not limited thereto. Preferable is a therapeutic drug for endometriosis because of the improved drug delivery to the local lesion according to the invention.

Examples of the therapeutic drug for endometriosis include danazol, nonsteroidal antipyretic and analgesic drugs, herbal drugs, progestogen, estrogen, GnRH-antagonists, gestrinone, antiestorogens, aromatase inhibitors and the like. Most preferable is danazol because a considerable drug efficiency can be expected when the drug is locally administered.

When the preparation according to the present invention contains danazol as a therapeutic drug for endometriosis, a preferable carrier may include hyaluronic acid, a salt thereof e.g. ammonium hyaluronate or sodium hyaluronate which have been chemically modified or not. These carriers can satisfactorily support danazol within a gel thereof and momentarily release the drug due to their superior responsibility to hyaluronidase or an active oxygen.

The preparation according to the present invention which comprises the therapeutic drug for endometriosis is applicable for both the internal endometriosis and the external endometriosis.

The subject to be administered the preparation according to the invention is not limited to human and may include female of mammal such as swine, cattle, horse, sheep, dog, cat, monkey or the like.

EXAMPLES

The present invention is concretely illustrated by the following Examples and Comparative Example, to which the invention is not limited.

Example 1

Manufacture of Monolayer Ring Preparations

To 900 mL of purified water, 5.4 g of sodium hyaluronate (CHA, an average molecular weight : 1,000,000, Chisso corp.; hereinafter referred to as "CHA") was dissolved. Separately, 7.41 g of distearyldimethylammonium chloride (hereinafter referred to as "DSC") was suspended in 1680 mL of purified water. Both the solution and the suspension were heated up to 45° C. Then, these were mixed with stirring and continued for 5 minutes. The resultant complex was recovered by centrifuging at 5,000 rpm at room temperature and washed with warm water at 45° C. After washing, the complex was lyophilized overnight and further vacuum-dried at 50° C. overnight to give 9.9 g of CHA-DSC complex. Yield: 85%.

The obtained CHA-DSC complex (9.0 g) was dissolved in the mixed solvent consisting of 200 ml of DMF, 3.0 g of acetic anhydride and 4.8 g of pyridine and then the suspension was stirred at room temperature overnight. 200 ml of water was added thereto under ice-cooling. Then, the resultant gel substance was recovered by the filtration and washed with water. After washing, the product was vacuum-dried at 50° C. overnight to give 8.5 g of acetylated CHA-DSC.

The amount of pyrogen in the acetylated CHA-DSC was determined as a content of endotoxin with the aid of Toxi-color system ES-6 and ET-2 sets (Seikagaku corp.). Consequently, the amount of the pyrogen in CHA as a raw material is 0.2 EU/mg, whereas the amount of-the pyrogen in the acetylated CHA-DSC is 0.02 EU/mg.

In 20 mL of ultrapure water, 1.0 g of danazol and 7.5 g of the acetylated CHA-DSC were suspended and the suspension was immediately poured into a mold. Then, the drying was carried out by a freeze dryer to afford two pieces of the desired monolayer ring preparations.

Content of danazol: 420 mg

Size: outside diameter 55 mm, thickness of the ring 9.6 mm

Example 2

Manufacture of Monolayer Ring Preparations

To 900 mL of purified water, 5.4g of sodium chondroitin sulfate C (Wako Pure Chemical Industries, Ltd.; hereinafter referred to as "ChSC") was dissolved. Separately, 14.8 g of distearyldimethylammonium choride (DSC) was suspended in 1680 mL of purified water. Both the solution and the suspension were heated up to 45° C. Then, these were mixed with stirring and continued for 5 minutes. The resultant complex was recovered by centrifuging at 5,000 rpm at room temperature and washed with warm water at 45° C. After washing, the complex was lyophilized overnight and further vacuum-dried at 50° C. overnight to give 15.1 g of ChSC-DSC complex. Yield: 87%.

The obtained ChSC-DSC complex (9.0 g) was dissovled in the mixed solvent consisting of 2L of DMF, 3 g of acetic anhydride and 4.8 g of pyridine and then suspension was stirred at room temperature overnight. 2L of water was added thereto under ice-cooling. Then, the obtained gel substance was recovered by filtration and washed with water. After washing, the product was vaccum-dried at 50° C. overnight to give 9.0 g of acetylated ChSC-DSC.

In 20 mL of ultrapure water, 1.0 g of danazol and 7.5 g of the acetylated CHA-DSC were suspended and the suspension was immediately poured into a mold. Then, the drying was carried out by a freeze dryer to afford two pieces of the desired monolayer ring preparations.

Content of danazol: 420 mg

Size: outside diameter 55 mm, thickness of the ring 9.5 mm

Example 3

Manufacture of T-shaped Preparations

In 5 mL of ultrapure water, 3.0 g of danazol and 7.5 g of the acetylated CHA-DSC prepared according to Example 1 were suspended and the suspension was immediately poured into a mold suitable for manufacturing monolayer T-shaped preparations. Then, the drying was carried out by a freeze dryer to afford ten pieces of the desired T-shaped preparations.

Content of danazol: 300 mg

Size: Vertical bar; length 32 mm, diameter 2.6 mm Transverse bar; length 36 mm, diameter 2.6 mm 66 Nylon filament; length 54 mm, diameter 0.285 mm

Example 4

Manufacture of IUD-like Ring Preparations

In 5 mL of ultrapure water, 3.0 g of danazol and 7.5 g of the acetylated CHA-DSC prepared according to Example 1 were suspended and the suspension-was immediately poured into a mold suitable for manufacturing IUD-like ring preparations. Then, the drying was carried out by a freeze dryer to afford ten pieces of the desired IUD-like ring preparations.

Content of danazol: 300 mg

Size: outer diameter 22 mm, thickness of the ring 3.0 mm

Example 5

Manufacture of Sheet Gel Preparations

To a vessel placed in a clean bench, 0.7 g of danazol, 1.13 g of sodium hyaluronate (CHA) and 50 mL of ultrapure water were added and mixed. After mixing, the mixture was poured into a mold suitable for manufacturing sheet gel preparations and then lyophilized to afford ten pieces of the desired sheet gel preparation Content of danazol: 70mg Size: width 20 mm, length 40 mm, thickness 5 mm.

Example 6

Manufacture of Spherical Gel Preparations

In 5 mL of ultrapure water, 3.0 g of danazol and 7.5 g of the acetylated CHA-DSC prepared according to Example 1 were suspended and the suspension was immediately poured into a mold suitable for manufacturing spherical gel preparations. Then, the drying was carried out by a freeze dryer to afford ten pieces of the desired spherical gel preparations.

Content of danazol: 300 mg

Size: diameter 25 mm

Example 7

Manufacture of Past Gel Preparations

To 350 mL of ultrapure water in a vessel placed in the clean bench, 3.0 g of danazol and 7.0 g of sodium hyaluronate (CHA) were added and mixed to afford the desired past gel preparations Content of danazol: 150 mg/g Comparative Example 1

Manufacture of Monolayer Ring Preparations

At room temperature, 0.7 g of danazol, 25 g of Silastic 382, 2 g of Polysorbate 80 and 0.4 g of the tin catalyst were mixed. The mixture was poured into the mold and stored at room temperature until solidifying the mixture to afford two pieces of the monolayer ring preparations.

Content of danazol: 350 mg

Size: outside diameter 55 mm, thickness of the ring 9.5 mm

Comparative Test

Determination of the Rate of Sustained Release

The rate of the sustained release of danazol from the preparation manufactured in Example 1 or Comparative Example 1 was measured by In vitro Texts as follows.

(1) In Vitro Test 1

For the first 10 days, the preparation manufactured in Example 1 or Comparative Example 1 was placed in 3 L of a phosphate buffer (0.14 mol/L, pH 7.4). Then, the preparation was transferred to 3 L of the same buffer containing a bovine testicular hyaluronidase (10 unit/ml), and placed for scores of days at 37° C. with stirring. During the test period, an amount of danazol daily released into the buffer was determined by liquid chromatography.

Consequently, the release of danazol from the preparation of Example 1 was scarcely detected for the first 10 days, but after transferring into the buffer containing hyaluronidase, the release was stably maintained at approximately 200 µg/day. In contrast, the release of danazol from the preparation from Comparative example 1 was continued at all times of the test.

(2) In Vitro Test 2

For the first 10 days, the preparation manufactured in Example 1 or Comparative Example 1 was placed in 3 L of the phosphate buffer (0.14 mol/L, pH 7.4) and then transferred to ferrous sulfate solution (5 mmol/mL). Then, the preparation was placed in purified water for 3 minutes, transferred to 3L of the same buffer containing hydrogen peroxide (1 mmol/L) and placed for scores of days at 37° C. with stirring. During the test period, an amount of danazol daily released to the buffer was determined by liquid chromatography.

Consequently, the release of danazol from the preparation of Example 1 was scarcely detected for the first 10 days, but after transfer to ferrous sulfate solution, the release was stably maintained at approximately 200 µg/day of the rate. In contrast, the release of danazol from the preparation from Comparative Example 1 was continued at all times of the test.

INDUSTRIAL APPLICABILITY

The pharmaceutical preparations for the treatment of gynecologycal diseases according to the present invention can effectively release the careered therapeutic drug by hyaluronidase or an active oxygen generated at the affected portion. Specifically, a biodegradable polymer as a carrier is preferably a chemically modified hyaluronic acid or a salt thereof prepared by O-acylating, alkoxylating or crosslinking a complex of hyaluronic acid or a salt thereof and a cationic compound in a nonaqueous solvent, because the polymer can provide a superior sustained releasing property of the desired drug in a body for a long term. Furthermore, the polymer contains a reduced amount of a pyrogen and an antigenic substance and thus there is concern with an adverse effect and its safety is ensured.

If the preparation for the treatment of gynecological diseases according to the invention is administered in the uterine cavity, the vagina the pelvic cavity, or the ovarian endometrioma of a patient, the carrier comprising a biodegradable polymer needs not be removed from the body after the completion of the release of the drug and thus the physical and mental burden of patients can be significantly decreased.

What is claimed is:

1. A pharmaceutical preparation for the treatment of gynecological diseases which comprises a therapeutic drug for the intrauterine, intravaginal or intrapelvic administration, or for the administration into the ovarian endometrioma and a biodegradable polymer comprising chemically modified hyaluronic acid or a salt thereof, wherein the chemically modified hyaluronic acid or a salt thereof is prepared by O-acylating a complex of hyaluronic acid or a salt thereof and a quaternary ammonium salt in a non-aqueous solvent and contains a decreased amount of a pyrogen and/or an antigenic substance, said amount has been decreased by the O-acylating in the non-aqueous solvent to the extent that the amount of the pyrogen is not more than 0.05 endotoxin unit (EU)/mg, and wherein the drug is supported by the biodegradable polymer as a carrier.

2. The pharmaceutical preparation as claimed in claim 1, in which the nonaqueous solvent is one or more solvents selected from the group consisting of chloroform, toluene, methylene chloride and heptane.

3. The pharmaceutical preparation as claimed in claim 1, wherein the biodegradable polymer is produced by O-acylating a complex of hyaluronic acid or a salt thereof and a quaternary ammonium salt by a step (i) O-acylating with an organic acid employing at least one acid catalyst selected from the group consisting of mineral acids, organic acids and Lewis acids, (ii) O-acylating with an organic acid employing at least one dehydrating agent selected from the group consisting of N,N'-dicyclohexylcarbodiimide, 2-chloro-1-methyl pyridiniumiodide and N,N'-carbonyl diimidazole, or (iii) O-acylating with employing an acid anhydride or an acid halide in the presence of an acid binder.

4. The pharmaceutical preparation as claimed in claim 1, wherein a weight ratio of the drug to the biodegradable polymer is in the range of 1:10 to 2:1.

5. The pharmaceutical preparation as claimed in claim 1, which is a T-shaped preparation and wherein a vertical bar has a length of 20 to 40 mm and a diameter of 1.0 to 3.0 mm and a transverse has a length of 25 to 45 mm and a diameter of 3.0 to 4.0 mm.

6. The pharmaceutical preparation as claimed in claim 1, which is IUD-like ring and wherein an outside diameter is in the range of 20 to 25 mm and a thickness is in the range of 2.5 to 4.5 mm.

7. The pharmaceutical preparation as claimed in claim 1, which is a sheet gel.

8. The pharmaceutical preparation as claimed in claim 1, which is a spherical form of which a diameter is in the range of 20 to 25 mm.

9. The pharmaceutical preparation as claimed in claim 1, which is a paste gel.

10. The pharmaceutical preparation as claimed in claim 1, wherein the drug is a therapeutic drug for endometriosis.

11. The pharmaceutical preparation as claimed in claim 1, wherein the therapeutic drug is danazol.

12. A method for treating a gynecological disease in a patient comprising administering to the patient a pharmaceutical preparation comprising a therapeutic drug and a carrier comprising a chemically modified hyaluronic acid or a salt thereof, wherein the chemically modified hyaluronic acid or salt thereof is prepared by O-acylating a complex of hyaluronic acid or a salt thereof and a quaternary ammonium salt in a nonaqueous solvent and contains a decreased amount of a a pyrogen and/or an antigenic substance, said amount has been decreased by the O-acylating in the nonaqueous solvent to the extent that the amount of the pyrogen is not more than 0.05 endotoxin unit (EU)/mg.

* * * * *

UNITED STATES PATENT AND TRADEMARK OFFICE
CERTIFICATE OF CORRECTION

| | | |
|---|---|---|
| PATENT NO. | : 7,041,310 B2 | Page 1 of 1 |
| APPLICATION NO. | : 10/108298 | |
| DATED | : May 9, 2006 | |
| INVENTOR(S) | : Yui et al. | |

It is certified that error appears in the above-identified patent and that said Letters Patent is hereby corrected as shown below:

On the Title page of the patent Item (73) Assignees: please insert the following

Kouichi Murakami, Ishikawa-ken (JP)

Signed and Sealed this

Fourth Day of September, 2007

JON W. DUDAS
*Director of the United States Patent and Trademark Office*